United States Patent [19]
Stoerker et al.

[11] Patent Number: 5,843,649
[45] Date of Patent: Dec. 1, 1998

[54] METHOD OF IDENTIFYING CLONAL CELL SAMPLES USING HETERODUPLEX GENERATORS

[75] Inventors: Jay Stoerker, Malvern, Pa.; Kenneth R. Shroyer, Aurora, Colo.

[73] Assignee: University of Colorado, Boulder, Colo.

[21] Appl. No.: 396,927

[22] Filed: Mar. 1, 1995

[51] Int. Cl.$^6$ .............................. C12Q 1/68; C12P 19/34; C07H 21/04

[52] U.S. Cl. ........................... 435/6; 435/91.2; 536/24.3; 536/24.31; 536/24.33

[58] Field of Search .............................. 435/6, 91.2, 810; 536/24.3, 24.31, 24.33

[56] References Cited

U.S. PATENT DOCUMENTS 5,459,039  10/1995  Modrich et al. ............................. 435/6

OTHER PUBLICATIONS

Corcoran, M. et al., "Methylation Analysis by Means of PCR SSCP: Application to Clonality Studies", *Nucleic Acids Res.* 1993, 21, 4655.

Gilliland, D.G. et al., "Clonality in Myeloproliferative Disorders: Analysis by Means of the Polymerase Chain Reaction", *PNAS USA* 1991, 88, 6848–6852.

Innis, et al. Eds., PCR Protocols: A Guide to Methods and Applications, Academic Press, Inc., San Diego, CA 1990.

O'Brien, S., Ed., "Genetic Maps: Locus Maps of Complex Genomes", Sixth Edition, pp. 5.129–5.175, Cold Spring Harbor Press, Cold Spring Harbor, New York, 1993.

Sarkar, G. et al., "The Megaprimer Method of Site–Directed Mutagenesis", *BioTechniques* 1990, 8(4), 404–407.

Shroyer, K. et al., "Analysis of Clonality in Archival Tissues by Polymerase Chain Reaction Amplification of PGK–1", *Human Pathology* 1994, 25(3), 287–292.

Enomoto, T. et al., "Analysis of Clonality by Amplification of Short Tandem Repeats. Carcinomas of the Female Reproductive Tract", *Diagnostic Molecular Pathology* 1994, 3(4), 292–297.

Mutter, G. et al, "A Polymerase Chain Reaction Assay for Non–Random X Chromosome Inactivation Identifies Monoclonal Endometrial Cancers", *Am. J. of Pathology* 1995, 146(2), 501–508.

Wood et al., *Lancet* 342, 1519–1520 (1993).

Kurman et al., *Cancer* 49, 2547–2559 (1982).

Doherty et al., *Proc. Amer. Assoc. Cancer Res. Ann. Meet.* 35(0), Abstract, 571 (1994; presented Apr. 10–13).

*Primary Examiner*—Kenneth R. Horlick
*Attorney, Agent, or Firm*—Clark & Elbing LLP

[57] ABSTRACT

Methods of distinguishing between neoplasms and pseudoneoplastic or hyperplastic processes are disclosed. The methods comprise first contacting DNA from cells of a tissue sample from a female individual with a cytosine-methylation specific endonuclease, generating amplified fragments of a cytosine-methylation regulatable polymorphic X chromosome gene using primers that bracket a restriction site of said cytosine-methylation specific endonuclease and a polymorphic sequence in said nucleotide sequence of the gene; generating heteroduplexes between amplified fragments and heteroduplex generators which consist of 1–5 nucleotide differences from the amplified fragments; and detecting the presence of a single species of heteroduplex or two species of heteroduplexes. The presence of a single species of heteroduplex which indicates amplified fragments from a clonal population of cells which is indicative a neoplasm and the presence of two species of heteroduplexes indicates amplified fragments from a mosaic population of cells is indicative a pseudoneoplastic or hyperplastic process. Reagents and kits for performing the methods are disclosed.

16 Claims, 6 Drawing Sheets

Digest control and tumor DNA with
methylation sensitive restriction endonuclease

↓

PCR amplification of X-linked target

↓

Hybridize PCR product with Heteroduplex
Generator

↓

Polyacrylamide gel electrophoresis

METHOD OF IDENTIFYING CLONAL CELL SAMPLES USING HETERODUPLEX GENERATORS

ACKNOWLEDGEMENT OF GOVERNMENT RIGHTS

This invention was made with support under Grant Number 1R55CA60830-01 awarded by the National Cancer Institute. The U.S. Government has certain rights in this invention.

FIELD OF THE INVENTION

The present invention relates to methods of determining-whether a tissue sample from a female individual contains a clonal population of cells and to kits and reagents useful for practicing the same.

BACKGROUND OF THE INVENTION

The histologic distinction between malignant and pseudo-malignant cellular proliferative processes may be difficult. For example, the distinction between endometrial hyperplasia with atypia and adenocarcinoma relies on subtle qualitative and quantitative changes, and the two often cannot be differentiated with absolute certainty. More objective data to support the diagnosis of a benign versus malignant proliferative process could be of great benefit in determination of prognosis and in guiding subsequent clinical management.

A wide variety of approaches including analysis of karyotypic abnormalities, gene rearrangements, oncogene and anti-oncogene mutations, and loss of heterozygosity have been utilized for the investigation of clonal composition in neoplastic tissues. Each of these methods, however, are potentially informative in only a subset of cases, typically including moderately and poorly differentiated tumors which are readily diagnosed as malignant by microscopic examination.

The somatic mutation theories of carcinogenesis are based on the hypothesis that neoplastic proliferations are composed of clonal cell populations. The most consistent marker of clonal composition in well differentiated tumors of women is uniformity of the pattern of X-chromosome inactivation. Such uniformity of X-chromosome inactivation is not found in mosaic populations of cells.

A variety of methods have been applied for the analysis of X-chromosome inactivation. The first studies were based on the analysis of glucose-6-phosphate dehydrogenase (G6PD) isoenzymes, which are heterozygous in only 2% of females, precluding widespread application of this approach. The subsequent development of methods for restriction fragment length polymorphism (RFLP) analysis have increased the effective level of heterozygosity for any one marker to about 30% of cases. However, RFLP, but like G6PD analysis, also requires fresh tissue.

Recent studies based on RFLP analysis of polymerase chain reaction (PCR) amplification products permit utilization of formalin-fixed archival tissue collections for the analysis of clonality. Other current methods include ligase chain reaction and amplification of the human androgen receptor repetitive sequence polymorphic site. While having a high rate of informativity, these methods are technically difficult and time consuming, again precluding their widespread application.

There is a need for an improved method of analyzing X chromosome inactivation patterns. There is a need for a fast, easy and accurate method of differentiating tissue samples with clonal cell populations from those with mosaic populations. There is a need for a fast, easy and accurate method of differentiating neoplastic lesions from pseudoneoplastic lesions.

SUMMARY OF THE INVENTION

The present invention relates to methods of identifying whether a tissue sample from a female individual is neoplastic or either pseudoneoplastic or hyperplastic. The methods comprise the steps of:

a) contacting DNA from cells of a tissue sample from a female individual with a cytosine-methylation specific endonuclease under digest conditions;

b) generating amplified fragments that consist of 50–2000 nucleotides by amplifying a nucleotide sequence of a cytosine-methylation regulatable polymorphic X chromosome gene of the DNA using primers that bracket a restriction site of the cytosine-methylation specific endonuclease and a polymorphic sequence in the nucleotide sequence of the gene;

c) generating heteroduplexes between amplified fragments and heteroduplex generators, wherein the heteroduplex generators consist of 1–5 nucleotide differences from amplified fragments; and d) detecting the presence of a single species of heteroduplex or two species of heteroduplexes, wherein the presence of a single species of heteroduplex indicates amplified fragments from a clonal population of cells which is indicative of a neoplasm and the presence of two species of heteroduplexes indicates amplified fragments from a mosaic population of cells which is indicative of a pseudoneoplastic or hyperplastic process.

The present invention relates to kits that comprise:

1) a container having primers which bracket a methylation sensitive restriction site on a methylation regulated polymorphic X chromosome gene, wherein an amplified fragment is generated when DNA from a female individual is used as a substrate for the primer in a polymerase chain reaction and 2) a container having a heteroduplex generator that forms heteroduplexes with said amplified fragment, said heteroduplex generator having no more than 5 nucleotide sequence differences from said amplified fragment.

BRIEF DESCRIPTION OF THE DRAWINGS

In FIG. 3A, note the back-to-back glands with modest nuclear atypia (H&E). FIG. 3B shows PCR amplification of PGK-1 and analysis by HG. Lanes 1, 3, 5 =control tissue (myometrium); lanes 2, 4, 6=tumor. Arrow indicates migration of amplification products at apparent molecular weight of 548 bp. Hybridization with the HG resulted in generation of four discrete heteroduplex bands (lanes 3, 4) Treatment of DNA with HpaII prior to amplification resulted in loss of two of the four heteroduplex bands from tumor (lane 6), but not control (lane 5), consistent with the clonal composition of the tumor. M, 100 bp ladder.

In FIG. 4A, note the epithelial crowding with mild nuclear atypia (H&E). FIG. 4B shows PCR amplification of PGK-1 and analysis by HG. Lanes 1, 3, 5 =control tissue (myometrium); lanes 2, 4, 6=hyperplasia). Arrow indicates migration of amplification products of apparent molecular weight 548 bp. Hybridization with the HG resulted in generation of four discrete heteroduplex bands (lanes 3, 4). Treatment of DNA with HpaII prior to amplification did not produce attenuation of any of the heteroduplex bands, consistent with polyclonal composition of both control tissue and tumor. M, 100 bp ladder.

In FIG. 5A, note the marked nuclear pleomorphism and abnormal mitotic figures (H&E). FIG. 5B shows PCR amplification of PGK-1 and analysis by HG. Lanes 1, 3, 5=control tissue (focally necrotic granulation tissue); lanes 2, 4, 6=tumor. Arrow indicates migration of amplification products at apparent molecular weight 548 bp. Hybridization with the HG resulted in generation of multiple heteroduplex bands of dissimilar intensity (lanes 3, 4). Treatment of DNA with HpaII prior to amplification resulted in anomalous patterns of reduction of heteroduplex bands (lanes 5, 6), suggestive of the presence of aneuploid cells in tissue from both control and tumor. M, 100 bp ladder. As shown in this figure, HG analysis is less valuable for poorly differentiated samples relative to the results seen above for well differentiated samples. This is due to the fact that poorly differentiated samples are indicative of extensively developed malignancy. Poorly differentiated malignant cells often degrade genetically. As shown in Table 4, cells for this sample had 0 or 1 X chromosome making the technique that is the present invention less effective. However, since poorly differentiated samples do not present diagnostic problems associated with well differentiated samples, these results do not diminish the overall usefulness of the invention.

DETAILED DESCRIPTION OF THE INVENTION

Figure 1:
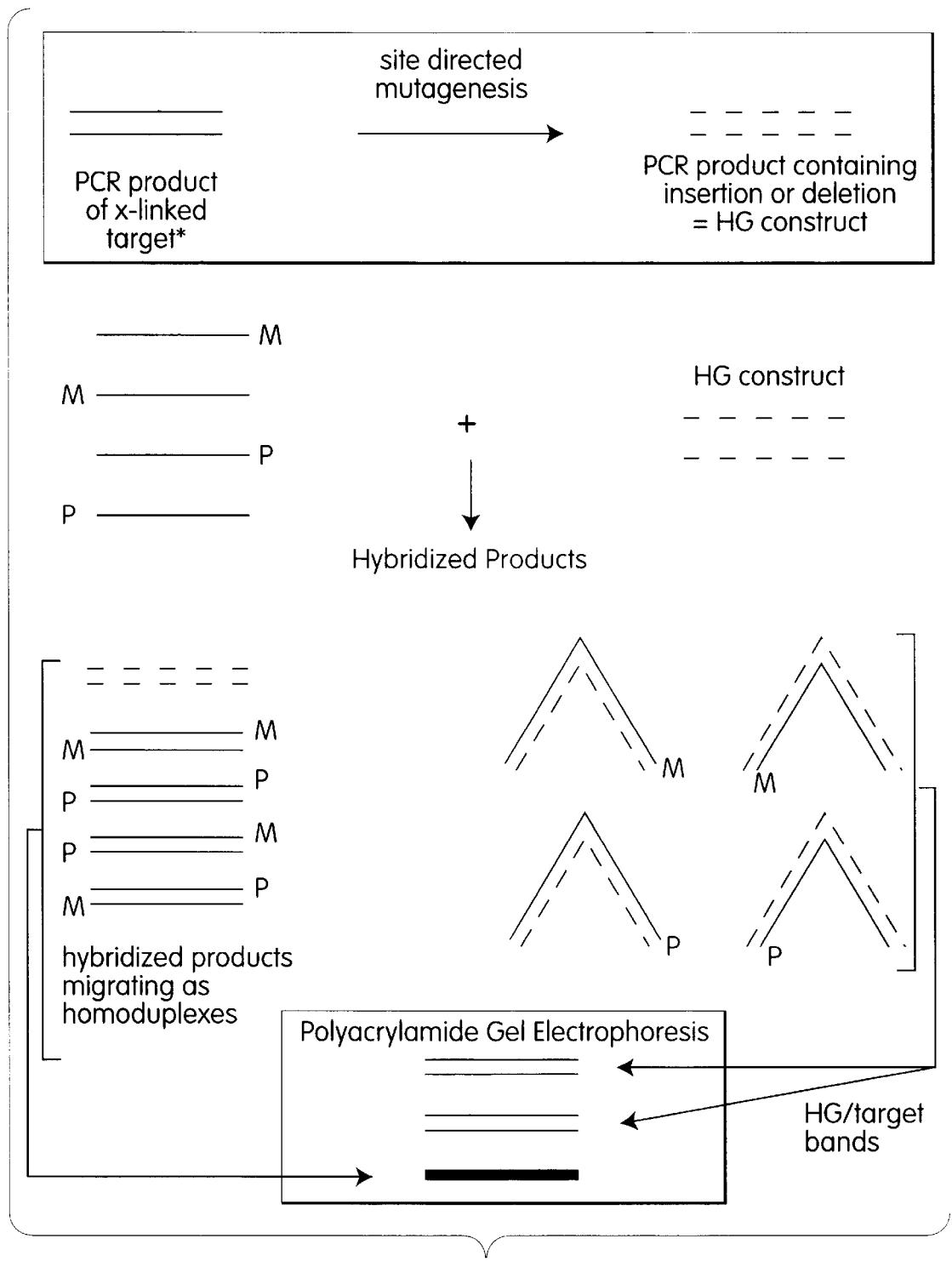
FIG. 1 shows the creation and use of heteroduplex generators (HG) for detection of X-linked polymorphisms. M is the amplification product of maternally derived X chromosome. P is the amplification product of paternally derived X chromosome. * is the amplified target containing a methylation sensitive restriction endonuclease site and a polymorphic site.

As used herein, the term "clonal population" is meant to refer to a population of cells from a sample of tissue from an individual that all display a uniform pattern of X-chromosome inactivation. Cells in a sample of tissue from a female with cancer are a clonal population.

As used herein, the term "mosaic population" is meant to refer to a population of cells from a sample of tissue from an individual that are a mixed population consisting of two cell types that differ from each other by which of the two X-chromosomes has been inactivated. Cells in a sample of tissue from a female with hyperplasia or other non-neoplastic processes are a mosaic population.

Neoplastic lesions can be differentiated from benign pseudoneoplastic lesions and hyperplastic lesions by determining whether or not a sample of cells contains a clonal or a mosaic population of cells.

As used herein, the term "X chromosome genes" is meant to refer to genes that occur on the X chromosome.

As used herein, the term "polymorphic genes" is meant to refer to alleles of a gene which have divergent nucleotide sequences including insertions, deletions and substitutions of one or more nucleotides relative to each other.

As used herein, the terms "polymorphic sequence" and "polymorphic site" are used interchangeably and are meant to refer to a nucleotide sequence which constitutes all or part of the divergent nucleotide sequences which characterize polymorphic genes. Polymorphic sequences may include nucleotide sequences of one allele of a gene which differs from the corresponding nucleotide sequences of another allele of that gene due to nucleotide insertions, deletions and/or substitutions of one or more nucleotides. Polymorphic sequences are the nucleotide sequences of polymorphic genes that make two alleles of the same gene different.

As used herein, the term "cytosine-methylated genes" is meant to refer to genes in which cytosine nucleotides are methylated. Nucleotide sequences which constitute restriction enzyme sites are cleaved by restriction endonucleases. Certain restriction endonucleases will not cleave a nucleic acid molecule with the proper restriction site if one or more cytosine nucleotides within the sequence are methylated.

As used herein, the term "methylation sensitive restriction endonucleases" is meant to refer to restriction endonucleases which do not cleave nucleic acid molecules at their restriction site on the molecule if one or more nucleotides in the sequence of the site are methylated.

As used herein, the term "methylation-regulated X chromosome genes" is meant to refer to X chromosome genes in which one copy is methylated as a means to activate or inactivate it. Some methylation-regulated genes are activated when methylated while others are inactivated by methylation.

As used herein, the term "methylation-inactivated genes" is meant to refer to genes that are inactivated by methylation.

As used herein, the term "methylation-activated genes" is meant to refer to genes that are activated by methylation.

Methylation inactivated genes on the inactivated X chromosome are methylated while the corresponding genes on the activated X chromosome are unmethylated. Methylation activated genes on the inactivated X chromosome are unmethylated while the corresponding genes on the activated X chromosome are methylated.

As used herein, the terms "amplified fragments" and "amplified products" are used interchangeably and are meant to refer to DNA molecules that are generated by amplification protocols such as PCR.

As used herein, the term "primers that bracket" is meant to refer to sets of primers in which one primer hybridizes to a sequence upstream (5') of a specific sequence, such as for example a restriction site or polymorphic sequence, and the other primer hybridizes to a sequence downstream (3') of the specific sequence such that amplification using such primers generates amplified products that contain the specific sequence.

As used herein, the terms "heteroduplex generators" and "HG" are used interchangeably and are meant to refer to nucleic acid molecules which are capable of hybridizing to PCR products of both polymorphic forms of an amplified gene wherein the HG are not fully complementary to one or more of the polymorphic isoforms. Preferably, the HG is not fully complementary to either of two polymorphic isoforms, and if there are more than two possible polymorphic forms, it is not fully complementary to any polymorphic form.

As used herein, the term "nucleotide sequences differences" as used to distinguish the nucleotide sequences of heteroduplex generators from the nucleotides sequences of amplified fragments is meant to refer to the non-complementary nucleotides in the two otherwise complementary nucleotide sequences. The nucleotide sequence differences between an HG and an amplified product may be one or more nucleotide insertions, deletions and/or substitutions to that sequence that is fully complementary to the sequence of the amplified product. The presence of the nucleotide sequence differences results in the formation of heteroduplexes between the two strands as opposed to homoduplexes.

As used herein, the term "a single species of heteroduplex" is meant to refer to a population of identical heteroduplexes. A population of identical heteroduplexes is formed using an HG when all amplified fragments are identical.

As used herein, the term "two species of heteroduplex" is meant to refer to a population of heteroduplexes formed from a mixed collection of amplified fragments in which some. e.g., half, have a particular nucleotide sequence and the remainder have a second and different nucleotide sequence.

As used herein, the term "digest conditions" is meant to refer to conditions in which a cytosine-methylation specific restriction endonuclease will cleave a DNA sequence that contains the sequence that constitutes a restriction endonuclease cleavage site recognized by that restriction endonuclease provided the cytosines in the sequence are not methylated.

The present invention provides a method for the analysis of patterns of X-chromosome inactivation, particularly using heteroduplex generators (HG). According to the present invention, the clonal composition of tissue samples, including but not limited to routinely fixed, paraffin embedded tissue samples, can be analyzed to provide for differential diagnosis or screening in cases where neoplastic lesions must be distinguished from pseudo-neoplastic or hyperplastic processes. Polymorphic X chromosome genes, particularly those for which heterozygote individuals are common or typical, are the subject of inactivation analysis. Inactivation pattern analysis is performed using methylation sensitive restriction endonucleases to cleave unmethylated but not methylated genes. Thus, the unmethylated allele of a heterozygous polymorphic X chromosome gene will be cut while the methylated form is protected from digestion by the enzyme and remains intact. PCR primers designed to selectively amplify the uncut form can generate multiple copies of the methylated allele of a heterozygous polymorphic X chromosome gene in a population of cells. Utilizing heteroduplex generators, a determination can be made whether or not the amplified sequences are all identical or contain different alleles. The presence of more than one allele in the amplified fragment indicates that a mosaic population of cells furnished the PCR substrate. The presence of a single allele in the amplified fragment indicates that a clonal population of cells furnished the PCR substrate if the individual is heterozygous.

The use of heteroduplex generators for analysis of PCR products is technically straightforward and rapid. The method eliminates the requirement of RFLP analysis of the amplified product and eliminates the requirements for radio-chemical incorporation, long electrophoretic gel runs and autoradiographical exposure, which are inherent in most alternative approaches, including analysis of short tandem repeats, the ligase chain reaction and single strand conformation polymorphism (SSCP) analysis.

The present invention relies on four specific phenomena to accomplish the fast, accurate and reliable method of identifying female individuals who have neoplasms and distinguishing such individuals from those who are exhibiting benign hyperplasias or pseudoneoplastic processes. The first phenomenon is the random inactivation of X chromosomes in populations of cells in a female individual. Although females have two X chromosomes, one is inactivated in every cell and the pattern of inactivation is a random event. Thus, clonal populations of cells can be distinguished from normal cells in a tissue sample because clonal cells will have the same X chromosome inactivated while normal cells will randomly have one or the other inactivated, resulting in a mixed population. Inactivation of genes is correlated with cytosine-methylation. Second, some genes on the X chromosome are polymorphic and many female individuals are heterozygous for such genes. In such individuals, one allele is activated and the other is inactivated. Third, certain restriction endonucleases that will cleave DNA at specific nucleotide sequences will do so if the DNA is not methylated. Such restriction endonucleases will not digest DNA with the same specific nucleotide sequences if the DNA is methylated. Finally, heteroduplex DNA migrates through electrophoresis matrices differently from identical sized homoduplex DNA and different species of heteroduplex DNA migrate uniquely relative to other identically sized heteroduplex DNA samples which differ by only 1–5 nucleotide differences. Heteroduplex DNA, including those having as many as 5 total nucleotide mismatches, insertions and deletions, migrates in distinct patterns relative to other heteroduplex DNA, having the same number of total nucleotide mismatches, insertions and deletions with different nucleotides. Accordingly, identically sized DNA molecules with sequence differences including single nucleotide differences can be distinguished from each other by forming duplexes between the sequence being tested and a synthetic DNA molecule that has deletions, insertions and/or substitution such that it is not a complete complement to the test sequence.

According to the present invention, the clonal composition of tissues is analyzed through the study of patterns of X-chromosome inactivation using polymorphic genes in heterozygous individuals as markers. Methylation sensitive restriction endonucleases provide the means to selectively cleave methylation activated/inactivated genes. PCR technology provides a means to amplify the uncleaved copies of the methylation activated/inactivated genes. By determining whether or not the amplified copies of polymorphic methylation activated/inactivated genes are identical to each other or the collection contains two isoforms, a determination can be made as to whether a tissue sample contains a clonal composition of cells or not, and therefore, whether the tissue is a neoplastic tumor or a pseudoneoplastic or hyperplastic process.

The invention utilizes the phenomenon of X chromosome activation/inactivation by methylation. Females have two X chromosomes and, therefore, two copies of each X chromosome gene. One X chromosome is from the mother (maternal X chromosome) and the other is from the father (paternal X chromosome). During early embryogenesis in the female, one of the two X-chromosomes in each cell is randomly inactivated, creating what is referred to as the Barr body. The pattern of X-chromosome inactivation is maintained consistent through subsequent cell divisions. Thus, non-neoplastic tissues of a 46XX female are mosaic, i.e. comprised of cells differing in which of the X-chromosomes has been inactivated. By contrast, clonal cell populations maintain a uniform pattern of X-chromosome inactivation as established in the single cell of origin.

According to the invention, polymorphic methylation-regulated X chromosome genes are analyzed in a sample of cells to determine whether the cells are clonal or a mosaic population. Polymorphic genes are used as targets for analysis because, through the random inactivation of X chromosomes, the polymorphic gene on one X chromosome is methylated and polymorphic gene on the other X chromosome is unmethylated. The selection of the gene that is methylated is random so that mosaic populations of cells contain both forms of the X chromosome (the paternal X and the maternal X) methylated and unmethylated. In contrast, the X chromosome that is methylated in clonal populations is always the same, i.e., the paternal X chromosome is always the methylated one and the maternal X chromosome is always the unmethylated one or vice versa.

Thus, a mosaic population of cells is not identical with respect to the methylation of the polymorphic gene while the cells of the clonal population are identical with respect to the allele that is methylated. By determining whether all methylated forms of the polymorphic gene are identical or if more than one form of the polymorphic gene is methylated, cell populations can be identified as clonal or mosaic.

To practice the invention, polymorphic methylation-regulated X chromosome genes are identified and cleaved with a methylation-sensitive restriction endonuclease. Since it is a methylation-regulated X chromosome gene, the copy of the gene on one of the X chromosomes will be methylated and the other copy of the gene which is on the other X chromosome will be unmethylated. The unmethylated copy of the gene is cut by the methylation-sensitive restriction endonuclease while the methylated copy of the gene is protected and remains intact.

PCR primers are designed so that only the uncleaved copy of the gene can be used as an amplification substrate. Accordingly, a set of PCR primers is provided that brackets the methylation sensitive restriction site. A set of PCR primers that bracket the methylation sensitive restriction enzyme cleavage site includes one primer that hybridizes to a sequence 5' to the cleavage site and one primer that hybridizes to a sequence 3' to the cleavage site. Thus, if the DNA molecule is cleaved by a restriction enzyme, it cannot be a substrate for amplification using the primers that bracket the cleavage site, and no amplification can occur using a set of primers that includes a primer which brackets the cleavage site. However, if the site has been methylated, it will not be cleaved, and the molecule can serve as a PCR substrate using the primers.

PCR using such primers amplifies only one of the alleles from each cell. If the cells in the sample are a mosaic population and the individual is heterozygous for a polymorphic gene, then the PCR fragments generated will be different. If the cells in the sample are a clonal population, then the PCR fragments generated will be identical even if the individual is heterozygous for a polymorphic gene.

The polymorphic methylation-regulated X chromosome genes useful as targets for analysis according to the invention must meet the following criteria: 1) they must be X chromosome genes; 2) their patterns of inactivation must correlate to methylation, i.e., they must be activated or inactivated by methylation; 3) they must be polymorphic and preferably the incidence of heterozygotes in the population must exceed 2%, preferably, 5%, more preferably, 30%; and 4) they must contain a methylation sensitive restriction endonuclease site within about 2000 base pairs from a polymorphic site, preferably less than 1000 base pairs from a polymorphic site, more preferably less than 100 base pairs from the polymorphic site.

Using information widely available to those having ordinary skill in the art, including information disclosed in the references set out below, those having ordinary skill in the art can generate amplified fragments of gene sequences that contain the polymorphic alleles. Examples of X chromosome genes that have patterns of inactivation correlated to methylation and that are polymorphic in at least 2% of the population include those listed in Genetic Maps: Locus Maps of Complex Genomes, Sixth Edition, S. O'Brien, Editor, Cold Spring Harbor Press, Cold Spring Harbor, N.Y. 1993, pp. 5.129–5.163 and Polymorphic PCR—Detectable Markers of Man, Cuticchia, A. J. et al., Eds., Genome Data Base, Johns Hopkins University School of Medicine and the Welch Medical Library, 1830 E. Monument Street, Baltimore Md. 21205, which are both incorporated herein by reference. The references contain lists of polymorphic markers for which large populations are known to be heterozygous. The sequences of these polymorphic genes are known and PCR primers can be readily designed to be used to generate amplified products that may be analyzed in accordance with the invention to determine clonality. PCR primers are set out in the references which are useful to generate amplified products. Amplified products can be tested to determine if they possess sequences that can be cleaved by cytosine-methylation sensitive restriction endonucleases. HG -may be designed in accordance with the invention to allow for HG analysis of those amplified fragments that contain cytosine methylation sensitive restriction endonuclease sites within about 2000 base pairs from a polymorphic site, preferably less than 1000 base pairs from a polymorphic site, more preferably less than 100 base pairs from the polymorphic site. In some preferred embodiments, X chromosome genes that have patterns of inactivation correlated to methylation and that are polymorphic in at least 2% of the population are selected from the group consisting of phosphoglycerate kinase-1 (PGK-1) and monoamine oxidase A.

Examples of cytosine methylation sensitive restriction endonucleases are listed in Table 1. In some preferred embodiments, HpaII is used to cleave the unmethylated X chromosome gene sequence that contains a cytosine-methylation sensitive restriction endonucleases.

Conditions for restriction enzyme digestion of DNA vary based upon the restriction enzyme used. Those of ordinary skill in the art can use the various different methylation sensitive enzymes under the proper conditions to digest DNA in the sample following the manufacturer's instructions for proper conditions. Generally, enzymes digest DNA at 37° C., and the amount of enzyme used to cut the amount of DNA present is usually the amount of enzyme needed to digest the DNA in 10 minutes to 3 hours, preferably in about 30 minutes.

Once a polymorphic methylation-regulated X chromosome gene is selected which meets the required criteria, PCR primers are designed to amplify gene sequences on the methylated allele but not the unmethylated allele. PCR primers are designed which bracket the methylation sensitive restriction endonuclease site on a polymorphic methylation-regulated X chromosome gene. The PCR primers are designed so that they will not be useful to amplify the methylated allele after the sample is digested with the methylation sensitive restriction endonuclease. In addition to bracketing the restriction site, the general rules for designing primers is that typical primers are 18–28 nucleotides in length having 50' to 60' g+c composition. The entire primer is preferably complementary to the sequence it must hybridize to. Preferably, primers generate PCR products of 100 base pairs to 2000 base pairs. However, it is possible to generate products of 50 base pairs to up to 10 kb and more. In some preferred embodiments, PCR primers are designed to amplify sequences from polymorphic methylation regulated X chromosome genes to produce DNA fragments between 50–150 nucleotides in length. In some preferred embodiments, PCR primers are designed to amplify sequences from polymorphic methylation regulated X chromosome genes to produce DNA fragments between about 100 nucleotides in length.

In some embodiments, two "rounds" of amplification are performed: a first round of amplification to generate multiple copies of a first amplified fragment which is directly amplified from chromosomal DNA and a second round to generate multiple copies of a second amplified fragment which is an amplified product of a sequence within the first amplified product. The primers used to generate the second amplified product are nested primers which hybridize to sequences on the first amplified fragment and thus use the first amplified product as a substrate. Multiple copies can be generated from each of the multiple copies of the amplified substrate, thereby resulting in much greater yields of the second amplification fragment as compared to the number of copies that would be generated if the second primers were used on the chromosome as the substrate instead of first amplifying the substrate.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of a genomic sequence, exponential amplification of a specific double-stranded product results. If only a single primer hybridizes to the nucleic acid target sequence, linear amplification produces single-stranded products of variable length. Those of ordinary skill in the art can routinely perform PCR using primers to amplify sequences within a substrate.

The present invention is performed using a sample of tissue obtained from tissue of a female individual which is suspected of being either a clonal neoplastic lesion or a pseudoneoplastic lesion.

Examples include any disease where a lesion with well differentiated cells must be analyzed to determine whether the tissue sample is a neoplasm or a pseudoneoplastic or hyperplastic process. By testing to determine if the cells of the tissue sample are a clonal population or a mosaic population, a determination can be made whether the sample is a neoplasm or a pseudoneoplastic or hyperplastic process, and a therapeutic course of action can be undertaken based upon the diagnosis made using the information obtained using the invention. The present invention provides methods, reagents and kits for differential diagnosis in cases where neoplastic lesions must be distinguished from pseudoneoplastic or hyperplastic processes. A list of applications of the methods of the invention is included in Table 2 which describes the pseudoneoplastic or hyperplastic conditions versus the neoplastic conditions which can be distinguished using clonality analysis according to the invention. In a preferred embodiment, lesions in the uterus which may be either well differentiated endometrial adenocarcinoma or endometrial hyperplasia with atypia are common examples of situations where a sample from a female may consist of clonal neoplastic cells or pseudoneoplastic cells and be distinguished by clonal analysis.

The kits and methods of the present invention may be used to distinguish clonal neoplastic cells from pseudoneoplastic cells and thereby allow for the determination of whether or not the female individual from whom the cells were taken has cancer or not.

Tissue samples may be obtained using routine pathology sample collection techniques well known to those having ordinary skill in the art. The procedures for obtaining tissue samples for analysis to determine whether the cells in the sample are cancerous are well known and routinely performed. Samples include but are not limited to resected tissue, biopsy needle samples and aspirant.

Tissue samples may be fresh or fixed such as formalin fixed, paraffin embedded tissue samples prepared on slides for visual inspection. Samples may be analyzed as fresh samples in which samples are prepared as sections and viewed. Fixed tissue samples may be used such as samples routinely prepared for visual inspection. The procedures for fixing and optionally staining tissue samples for analysis to determine whether the cells in the sample are cancerous are well known and routinely performed.

DNA may be extracted from cells in tissue samples, or the restriction digest and PCR steps may be performed in cellular material. The procedures for amplifying sequences of genomic DNA in tissue samples, including fixed cells on slides, are well known and routinely performed. PCR amplification techniques are well known and are described in PCR *Protocols: A Guide to Methods and Applications,* Eds: Innis et al. Academic Press, Inc. San Diego Calif. 1990, which is incorporated herein by reference in its entirety. Techniques for amplification of DNA sequences using fresh samples are taught on pages 146–152. Techniques for amplification of DNA sequences using paraffin embedded samples are taught on pages 153–158. Use of PCR in diagnostic applications are taught in Part 4, Chapters 39–50.

Heteroduplex analysis using HG may be performed using a routinely applied protocol. HG are designed to hybridize to the amplified DNA but not to be 1000 complementary to it. That is, typically the HG is no more than 5 base pairs longer or shorter than the amplified fragment and has a complementary nucleotide sequence except for differences in sequence that include no more than a total of 5 consecutive nucleotide differences. HG are designed to contain one or more of the following differences from one and preferably both of the amplified fragments which may be generated by amplification of a polymorphic gene: a single mismatch, multiple mismatches, single insertions, multiple insertions, single deletions, multiple deletions or combinations of one or more of the above differences. Multiple mismatches are generally 2–5 nucleotides. Multiple insertions are generally 2–5 nucleotides. Multiple deletions are generally 2–5 nucleotides. HG are typically the same size as the PCR fragment they are to hybridize to, less any deletions and plus any insertions. Accordingly, HG are about 100 base pairs to 2000 base pairs. In some embodiments, they are 50 base pairs, 1000 base pairs or up to 10 kb and more.

HG analysis is performed as follows. Duplexes are formed by the addition of the HG to the amplified DNA. Generally, the ratio of HG to amplified fragment is between 5:1 and 1:5, preferably 1:1. In some preferred embodiments, HG are combined with amplified fragments at about 950 for about 5 minutes, followed by about 10 minutes at about 800, followed by slow cooling for about 30 minutes to about 500. If the HG is different from the amplified DNA from both polymorphic alleles, heteroduplexes will be generated. If the HG is different from the amplified DNA from both polymorphic alleles, and the sample contained a clonal cell population and thus a single allele to be amplified, a single species of heteroduplexes will be generated. If the HG is different from the amplified DNA from both polymorphic alleles, and the sample contained a mosaic cell population and thus two different alleles to be amplified, two species of heteroduplexes will be generated.

Heteroduplexes formed between an HG and different amplified DNA polymorphic forms, i.e., different species of heteroduplexes, will migrate differently in electrophoresis matrices such as precast 4–20% gradient polyacrylamide gels (Novex, San Diego, Calif.), PCR Purity Plus™ polyacrylamide gels (A. T. Biochem. Malvern, Pa.) or agarose gels (4% NuSieve, FMC Biproducts, Rockland, Me.). Samples which contain two species of heteroduplexes are distinguishable by gel electrophoresis migration patterns from single species of heteroduplexes formed between an HG and identical amplified DNA polymorphic forms. Accordingly, HG analysis allows for the rapid, reliable determination of whether all molecules in a sample of amplified DNA are identical or if the molecules were produced by amplification of two different substrates with differences of as little as a single nucleotide substitution, deletion or insertion. The migration pattern of duplexes formed using an HG with a sample of amplified DNA when all molecules in a sample of amplified DNA are identical is different from the migration pattern of duplexes formed using the same HG if the molecules were produced by amplification of two different substrates with differences of as little as a single nucleotide substitution, deletion or insertion. Thus, HG analysis can be used to determine if the amplified DNA was produced from DNA of a clonal cell population or a mosaic population of cells.

To detect whether the migration pattern of a duplex is due to a single, identical amplification product or a mixed amplification product, controls may be used to generate migration patterns using known duplex components. For example, controls can include, independently, heteroduplexes between: the HG and a sample that consists of only one of the two possible amplification products; the HG and a sample that consists of only the other one of the two amplification products; the HG and a sample that consists of both of the possible amplification products. One or more of such controls can be run as separate lanes next to test assay lanes on an electrophoresis matrix such as a precast 4–20% gradient polyacrylamide gel (Novex, San Diego, Calif.) or the like, a PCR Purity Plus' polyacrylamide gel (A. T. Biochem. Malvern, Pa.) or the like, or an agarose gel such as a 4- NuSieve gel (FMC Bioproducts, Rockland, Me.) or the like, which are useful to produce distinctive migration patterns for different species of heteroduplexes. Alternatively, the various migration patterns of the above-described controls can be presented in the form of a photograph, that optionally includes size markers, which can be used for comparison to the migration pattern observed using heteroduplexes formed between HG and the amplification product of DNA from cells of a tissue sample.

The present invention relates to kits for performing methods of the invention. Kits include: 1) a container having the primers which bracket a methylation sensitive restriction site on a methylation regulated polymorphic X chromosome gene; and 2) a container having an HG that hybridizes and forms heteroduplexes with the amplification products that are generated by PCR of the methylation regulated polymorphic X chromosome gene sequence using the primers of the kit, the HG having no more than 5 nucleotide sequence differences from either or both of the possible amplification products. Many sets of PCR primers which can be included in kits of the invention are disclosed herein. In addition, design of other sets of PCR primers useful to practice the invention can be routinely designed and synthesized in accordance with the invention.

Optionally kits can also include one or more of the following: 1) a container of cytosine-methylation sensitive restriction endonuclease which can cut the unmethylated allele of the methylation regulated polymorphic X chromosome gene at the cytosine-methylation sensitive restriction endonuclease restriction site that is bracket by the PCR primers of the kit; 2) matrix material in the form of an intact matrix or materials useful for producing the same which can be used to form the matrix through which the heteroduplexes are migrates; and/or 3) instructions for performing the method that is the invention. Moreover, kits may also optionally contain one or more of the following controls: 1) a container with the HG and a sample that consists of only one of the two possible amplification products; 2) a container with the HG and a sample that consists of only the other one of the two amplification products; 3) a container with the HG and a sample that consists of both of the possible amplification products; and/or 4) size markers. Kits may optionally contain photographs of migration patterns produced by controls and/or photographs of expected results or representative examples of one or more possible results which can be compared to the actual results to determine whether the sample contains a clonal or mosaic population.

EXAMPLE

METHODS

Sample Preparation and DNA extraction

Thirty-seven patients diagnosed with uterine endometrioid adenocarcinoma over an eight year period (1984–1992) were identified through the Colorado Central Cancer Registry. Tumors were classified and graded using standard diagnostic criteria. The patients ranged in age from 40 to 80 years at the time of diagnosis (mean age 63.5 years). Hematoxylin and eosin stained tissue sections from the formalin-fixed, paraffin-embedded tissue blocks were examined to identify areas where the lesional cells comprised greater than 50% of the total cell population. Microdissection of lesional cells was performed on 4 µm thick hematoxylin and eosin stained sections, under 50% (v/v) aqueous glycerol, using a 28 g hypodermic needle (Becton Dickinson, Franklin Lakes, N.J.) attached to a Leitz (Wetzlar, Germany) micromanipulator and a hand-held 2.0 µl glass pipette (Drummond Scientific, Broomwall, Pa.) with vacuum control. Quantitative assessment by microscopic examination of 100 cells showed that greater than 90% of cells collected from lesional tissue consisted of the intended target epithelial population. DNA of lesional cells and control tissue (benign myometrium) was deparaffinized and the DNA was extracted by Proteinase K digestion, according to standard protocols. Following digestion, the DNAs were extracted with phenol, ethanol precipitated, redissolved in $H_2O$, and the DNA content was measured spectrophotometrically (Beckman DU-50, Fullerton, Calif.).

Restriction Endonuclease Digestion

For the analysis of clonality, 1.5 microgram aliquots of genomic DNA were digested for 12 h at 37° C. with an excess (1.5–20 units) of HpaII methylation sensitive restriction endonuclease (Boehringer Mannheim GmbH, Germany) in 2.5 Al of incubation buffer (10MM Tris-HCl, 10 mM MgCl2, 1 mM dithioerythritol, pH 7.5 at 37° C.) with a final reaction volume of 25 µl.

Polymerase Chain Reaction Amplification

The PGK-1 gene is disclosed in Gilliland D. G. et al. Proc. Natl. Acad. Sci. USA 1991 88:6848–52, which is incorporated herein by reference. Amplification of a portion of the PGK-1 gene, including exon I was performed using nested primers: 1A=SEQ ID NO:1; 1B=SEQ ID NO:2; 2A=SEQ ID NO:3; and 2B=SEQ ID NO:4. Up to 0.6 micrograms of each DNA sample were amplified in a 100 µl reaction volume using a DNA thermal cycler (Model 480, Perkin-Elmer Cetus, Norwalk, Conn.) for 30–60 cycles using primers 1A, 1B (PGK-1 nucleotides 418–1180). Ten microliters of the amplified product were subsequently amplified using nested primers, 2A, 2B (PGK-1 nucleotides 5(-) I-1090) over an additional 30–60 cycles. Reagent controls lacking template DNA were carried through the amplification process to monitor for sample contamination. Adequacy of amplification was assessed by agarose gel electrophoresis (4% NuSieve, FMC Bioproducts, Rockland, Me.) and ethidium bromide staining of the gel.

Restriction Fragment Length Polymorphism Analysis

Aliquots (10 µl) of the PCR amplification product were incubated with 10U of BstX1 restriction endonuclease (Boehringer Mannheim, Indianapolis, Ind.) and evaluated for heterozygosity by polyacrylamide gel electrophoresis as previously described in Shroyer K. R. and E. G. Gudlaugsson (1994) *Hum. Pathol.* 25:287–92.

Construction of the Heteroduplex Generator

The heteroduplex generator (SEQ ID NO:5) was created through the site directed mutagenesis method as described by Sarkar T. G. and S. S. Sommer (1990) *BioTechniques* 8:404–7. Using amplified product from a male as template, another PCR was performed using a mutagenic primer (deleting bases TAG from coordinates 983–986 of the Gilliland sequence) and primer 2B, generating a 102 bp product. This product was then used as a primer in a subsequent PCR amplification with 2A, again using the amplified male DNA as template. After 16 cycles, primer 2B was added to the reaction. The product of this reaction was 527 bp long. A third PCR, using primers 2A and 2B, was performed to increase the concentration of product. All amplifications were performed using Vent™ (exo-) DNA polymerase (New England Biolabs, Beverly, Mass.). The resulting product was ligated into pT7 Blue (Novagen, Madison, Wis.). This was cloned into *E. coli* strain JM109. The heteroduplex generator was made by amplification of this clone with primers 2A and 2B.

PGK Heteroduplex Analysis

Figure 2:
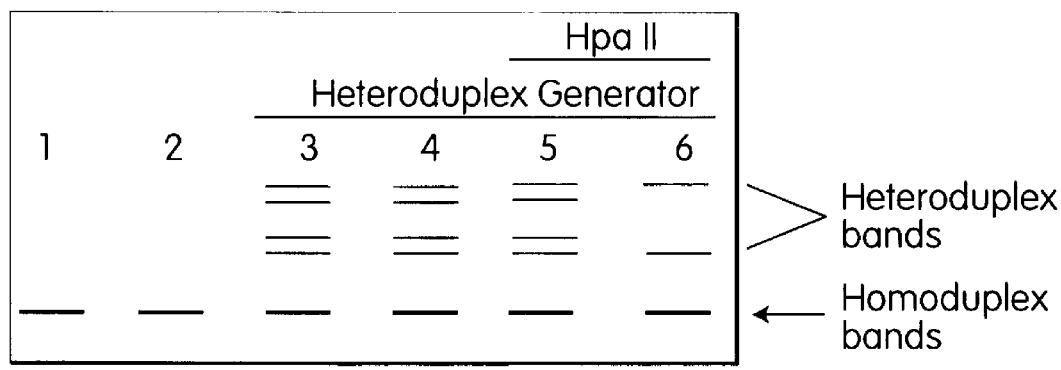
FIG. 2 shows a heteroduplex generator analysis of clonality. PCR amplification of phosphoglycerate kinase-1 (PGK-1) produces a single 530 bp product from either control myometrium (C, lane 1) or tumor (T, lane 2) genomic DNA. Hybridization of the PCR products with the HG (lanes 3, 4) results in the formation of homoduplex products which comigrate at 530 bp and 4 discrete heteroduplex bands which show markedly decreased mobility on polyacrylamide gel electrophoresis. Pretreatment of genomic DNA with HpaII has no effect on the heteroduplex band pattern from control tissue (lane 5) but blocks amplification of 2 of the 4 heteroduplex bands from tumor (lane 6).

Amplified DNA from lesional cells and control myometrium was hybridized with the PGK HG (FIG. 1) using a thermal ramp consisting of 95° C. in 1 second, 95° C. for 5 minutes, 80° C. in 1 second, 80° C. for 10 seconds, 30° C. in 30 minutes, 30° C. for 5 minutes. The hybridized products were analyzed by electrophoresis in 0.1M boric acid, 0.1M Tris, 2 mM EDTA and ethidium bromide staining using either a precast 4–20% gradient polyacrylamide gel (Novex, San Diego, Calif.), or PCR Purity Plus™ polyacrylamide (A. T. Biochem. Malvern, Pa.), with equivalent results. A schematic summary of the HG method for clonality analysis is shown in FIG. 2. The sensitivity of the method to detect a clonal population of cells was tested using DNA from a case which showed complete elimination of 2 of the 4 heteroduplex bands following amplification of HpaII pretreated genomic DNA. DNA from tumor cells was combined with DNA from the same patient's control tissue in varying proportions and processed for PGK HG analysis as described above. Following electrophoresis the hybridized products were visualized by silver staining according to routine protocols.

Fluorescence in situ Hybridization

FISH procedures in paraffin-embedded tissue sections were performed with a chromosome X alpha-satellite (DXZ1) probe according to the recommendations of the supplier (ONCOR, Gaithersburg, Md.). Hybridization signals were evaluated using a Zeiss AXIOSKOP microscope with a dual-pass filter for fluoroisothiocyanate and Texas red at 1000× magnification. For each sampler the number of hybridization signals per nucleus was determined in 100 consecutive qualifying interphase nuclei in at least four different areas of the same slide. Nuclei with disrupted membranes and nuclei which overlapped other nuclei were not scored. Nuclei were photographed using a Zeiss MC100 spot microphotographic system.

RESULTS AND DISCUSSION

A total of 37 cases originally diagnosed as endometrioid adenocarcinoma were entered into the study. PCR was successful in amplification of the PGK-1 target in 36/37 cases. HG analysis of 36 cases demonstrated heterozygosity in 12 cases (33.3%). These same 12 cases were also shown to be heterozygous by BstXI RFLP analysis of the PGK-1 amplification product. No additional polymorphisms were identified by the HG in BstXI RFLP negative cases. Amplified product for clonality analysis was obtained from both control and lesional tissues in 10 of 12 cases (Table 3), including 3 cases of well differentiated carcinoma, 5 cases of moderately differentiated carcinoma, and 2 cases of poorly differentiated carcinoma (Table 3).

Figure 3A:
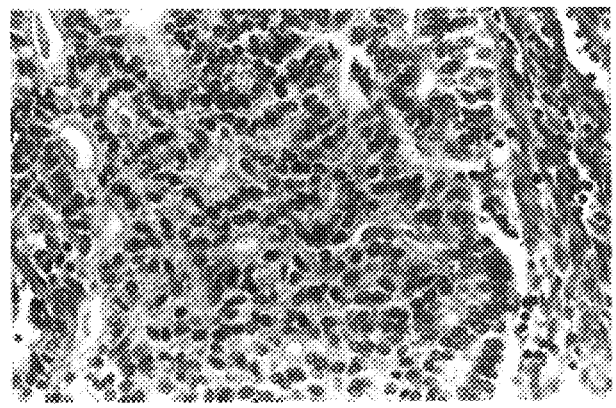
FIGS. 3A and 3B show a clonal analysis of a well differentiated endometrial adenocarcinoma representative case (case B).
Figure 3B:
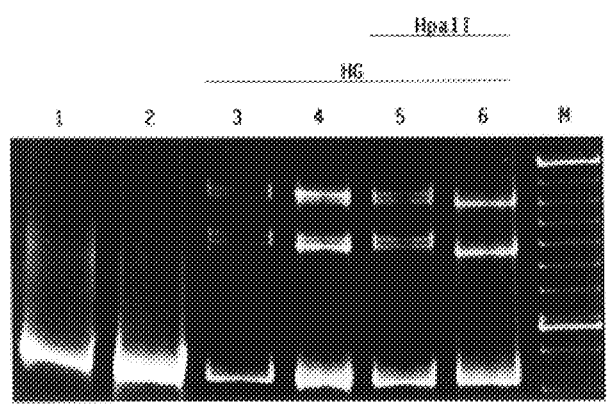
Figure 4A:
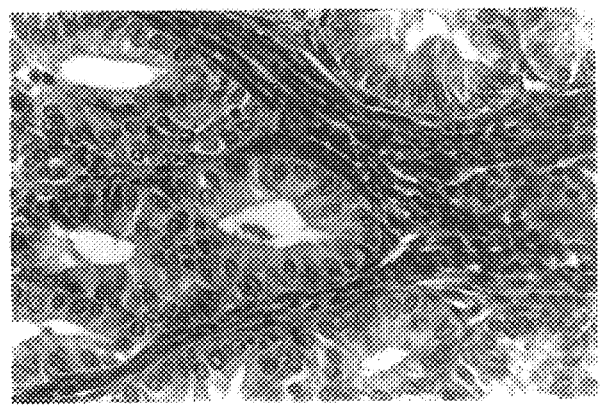
FIGS. 4A and 4B shows a clonal analysis of a sample that contains a mosaic cell population representative case (case G) The original diagnosis of this sample was well differentiated endometrioid adenocarcinoma. However, the present data indicates that the sample is pseudoneoplastic.
Figure 4B:
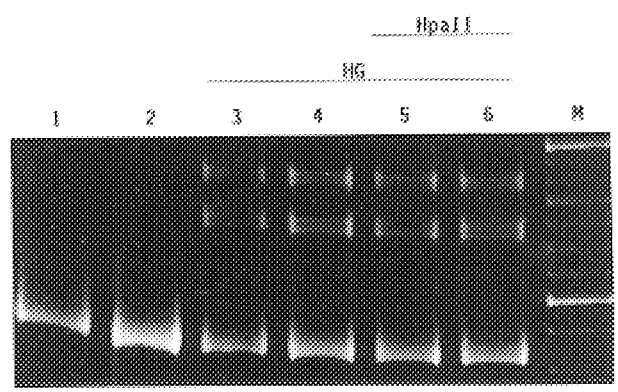

HG analysis of PGK-1 PCR amplification products from HpaII treated genomic DNA demonstrated clonal composition of cells in 7 of the 10 informative cases (FIG. 3). Clonal cases included 1 case of well differentiated carcinoma, 5 cases of moderately differentiated carcinoma, and 1 case of poorly differentiated carcinoma. HG analysis of cases G and I demonstrated polyclonal composition of the lesional tissue (FIG. 4). Both polyclonal cases were diagnosed as well differentiated carcinomas without evidence of myometrial invasion.

Figure 5A:
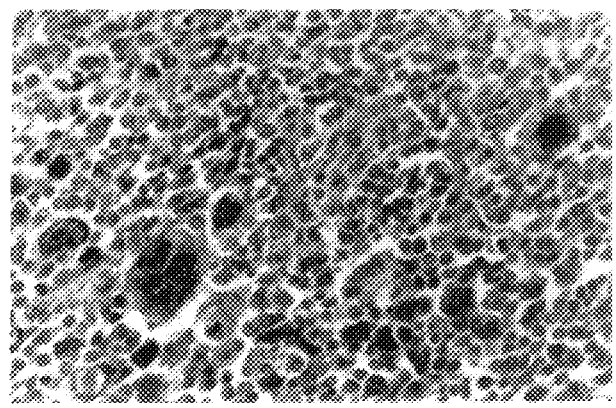
FIGS. 5A and 5B show a clonal analysis of a poorly differentiated endometrioid adenocarcinoma (case C).
Figure 5B:
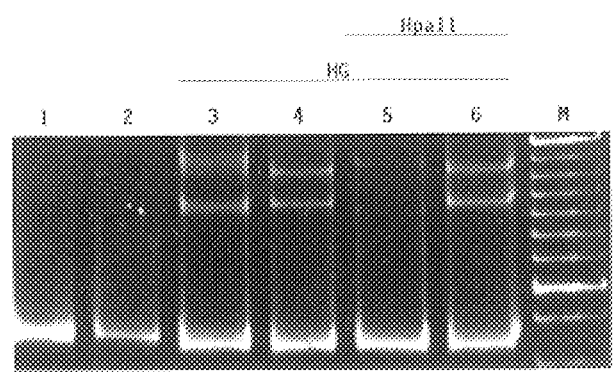

HG analysis in case C suggested an anomalous pattern of X-chromosome inactivation in both tumor and control tissue (FIG. 5). Among the 10 informative cases, case C was the only one which has shown evidence of metastatic dissemination. Review of the histopathologic features of this poorly differentiated carcinoma revealed extreme nuclear pleomorphism and numerous abnormal mitotic figures, strongly suggestive of aneuploid X-chromosome content. The control in this case showed myometrium with focally necrotic granulation tissue and scattered highly atypical cells, suspicious for infiltrative tumor cells. FISH analysis of case C, using an alpha-satellite probe for the X-chromosome (DXZ1), demonstrated hypodiploid X-chromosome content in a high proportion of both tumor cells and in atypical cells present in granulation tissue which was used as the control tissue (Table 4).

Figure 6:
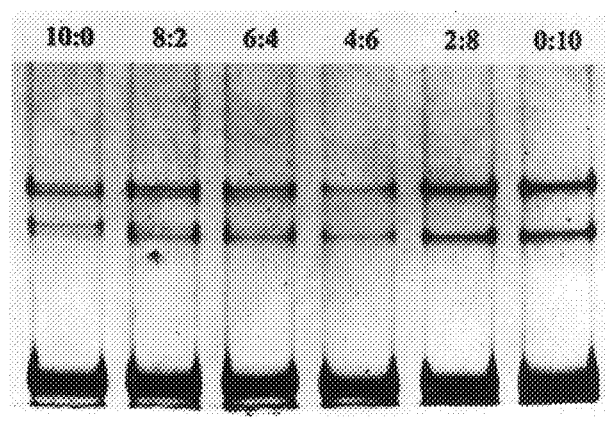
FIG. 6 demonstrates the sensitivity of HG analysis for detection of clonality. Genomic DNA from tumor (case A) was combined with DNA from normal tissue of the same patient in the proportions of 10:0, 8:2, 6:4, 4:6, 2:8 and 0:10 (normal:tumor) This was follows by HpaII digestion, PCR amplification of PGK-1 and analysis by HG, and silver staining of the polyacrylamide gel. Differences in the intensity of the heteroduplex bands was clearly distinguishable to the proportion of 4:6 (normal:tumor).

The sensitivity of HG analysis for the detection of clonal cell populations was tested on samples prepared by combining DNA derived from tumor with DNA derived from control normal tissue. Genomic DNAs were combined in the proportion of 10:0, 8:2, 6:4, 4:6, 2:8 and 0:10 (normal:tumor). Following HpaII digestion, PGK-1 PCR amplification and HG analysis was performed. As shown in FIG. 6, a clonal pattern of X-chromosome inactivation was clearly evident when the tumor cells comprised at least 60% of the total cell population in the tissue sample.

Twenty-nine of the 36 PCR amplifiable cases in the current study were included in a previous study of clonality. HG analysis detected eight PstXI polymorphisms in this subset. Five of these had been detected in the earlier study, and the remaining three were shown to be heterozygous by repeated BstXI RFLP analysis. This reflects the difficulty of determining clonality from RFLP analysis of PCR products due to the presence of heteroduplexes. While 50' of amplified products will contain the polymorphic restriction endonuclease site, only 25 will form homoduplexes which can be cleaved by the enzyme. Thus, even in normal issue with complete digestion of the PCR product, the uncleaved band will appear approximately 3 fold more intense than the primary cleaved band upon electrophoretic analysis. By contrast, HG analysis results in uniform band intensities for products of both maternally and paternally derived alleles from normal tissue. This greatly facilitates the detection of non random patterns of X-chromosome inactivation, as a marker of the presence of a clonal cell population.

No cases which contained a HG polymorphism were found which lacked a BstXI polymorphism. This suggests the absence of additional polymorphisms in the amplified sequence, since the HG would be predicted to detect other nucleotide sequence polymorphisms. The results are similar to those obtained using SSCP analysis (Corcoran M. M., et al. (1993) *Nucl. Acids Res.* 21:4655). SSCP analysis showed heterozygosity of the PGK-1 amplification products in 14 of 14 cases which were heterozygous for the BstXI RFLP, but did not detect any additional polymorphisms in any of over thirty cases which lacked the BstXI polymorphism. However, the HG approach is technically less demanding than SSCP analysis because it does not require high resolution electrophoresis.

The parameters for PCR amplification of PGK-1 are unusual, often requiring a nested primer approach with up to 120 combined cycles to produce clearly visible PCR product. The PGK-1 PCR amplification target contains a relatively high GC content, with up to 19 consecutive GC bases, which may explain the low level of sensitivity of amplification for this target. It is also likely that DNA extracted from archival formalin-fixed tissue is somewhat degraded and thus is an intrinsically difficult amplification target. Any PCR based, assay of X chromosome inactivations is dependent on a balanced amplification efficiency between the maternally derived and paternally derived alleles. Since an imbalance of amplification efficiency would be magnified through increasing cycles of amplification, an ideal target would require the least possible number of rounds of amplification.

The differential diagnosis between atypical hyperplasia and well differentiated adenocarcinoma of the endometrium is often difficult due to subtle qualitative and quantitative features which are used for the distinction between these entities. In terms of impact on the patient, it is imperative to be as accurate as possible in the diagnosis of carcinoma. In the current study, 2 of 3 cases diagnosed as well differentiated endometrioid adenocarcinoma were found to be composed of polyclonal cell populations. The 2 polygonal cases showed no evidence of myometrial invasion, raising the possibility that they could represent pseudoneoplastic proliferative processes. It is also possible that these cases represent technical failures of the PCR-based clonality assay. Since our mixing study indicated that the method can detect the presence of a clonal cell population in a background of up to 40% normal cells, however, it seems unlikely that these results were caused by contamination of the sample with DNA from non-neoplastic components of the tissue. While large studies of clonality correlating results with clinical outcome assessment, will be required, these preliminary results suggest the potential of clonality analysis as an aid for diagnostic purposes.

TABLE 1

Cysosine methylation sensitive restriction endonucleases

Group I cleavage blocked at all sites

Aat II
Aci I
Age I
Aha I
Asc I
Ava I
Bal I
BsaA I
BsaH I
BsiE I
BsiW I
BspD I
BsrF I
BssH I
BstB I
BstU I
Cfr 10 I
Cla I
Eag I
Eco 47 III
EcoR II
Esp3 I
Fsp I
Hae I
Hga I
Hha I
HinP1 I
Hpa II
Kas I
Mlu I
Msc I
Nae I
Nar I
NgoM I
Not I
Nru I
PflM I
Pml I
PpuM I
Pvu I
RsrI I
SacI I
Sal I

TABLE 1-continued

Cysosine methylation sensitive restriction endonucleases

ScrF I
Sma I
SnaB I
Stu I

Group II cleavage blacked at sites only with specific CG contexts

Acc I
Acc65 I
AlwN I
Apa I
ApaL I
AvaI I
Bae I
Ban I
BsaB I
Bsg I
Bsl I
BsmA I
Bst107 I
Drd I
Eae I
Ecl136 II
Eco0109 I
Hpa I
Nhe I
Rsa I
Sau3A 1
Sau96 I
Sfi I

TABLE 2

Pseudoneoplastic or hyperplastic conditions versus neoplastic conditions must be distinguished from each other in diagnosing female individuals with lesions. A list of applications of the methods of the invention is included in Appendix B which describes the conditions which can be distinguished from each other using clonality analysis according to the invention.

| | |
|---|---|
| 1. | Atypical nevus vs. melanoma |
| 2. | Actinic keratosis vs. squamous cell carcinoma |
| 3. | squamous hyperplasia of oral mucosa vs. squamous cell carcinoma |
| 4. | Verrucous hyperplasia vs. verrucous carcinoma |
| 5. | Pituitary hyperplasia vs. pituitary adenoma |
| 6. | Parathyroid hyperplasia vs. parathyroid adenoma |
| 7. | Adenomatoid change in colloid goiter vs. follicular carcinoma of thyroid |
| 8. | Cervical dysplasia vs. cervical carcinoma in situ |
| 9. | Reactive atypia or glandular dysplasia vs. colonic adenocarcinoma |
| 10. | Granulation tissue vs. carcinoma |
| 11. | Nodular fascitis vs. sarcoma |
| 12. | Endometrial hyperplasia vs. endometrial adenocarcinoma |
| 13. | Metastatic tumors vs. multiple independent primary tumors. |
| 14. | Adrenal cortical hyperplasia vs. adrenal cortical adenoma or adenocarcinoma |
| 15. | Endosalpingrosis vs. metastatic papillary seroces adenocarcinoma |
| 16. | Focal nodular hyperplasia of liver vs. hepatic adenoma or hepatocellular carcinoma |
| 17. | Chronic pancreatitis with reactive atypia vs. pancreatic adenocarcinoma |
| 18. | Cholangiocarcinoma vs. reactive atypia of ductal epithelium |
| 19. | Atypical ductal hyperplasia vs. ductal carcinoma in situ of breast |
| 20. | Atypical lobular hyperplasia vs. lobular carcinoma in situ |

TABLE 3

Analysis of clonality in endometrial hyperplasia and carcinoma

| Case | Year collected | Tissue diagnosis | Myometrial invasion | Metastatic dissemination[a] | Hpa II monoclonal[c] |
|---|---|---|---|---|---|
| A | 1989 | Uterus, endometrioid adenocarcinoma (grade II/III) | – | – | + |
| | | Uterus, benign myometrium | | | – |
| B | 1992 | Uterus, endometrioid adenocarcinoma (grade I/III) | + | – | + |
| | | Uterus, benign myometrium | | | – |
| C | 1984 | Uterus, endometrioid adenocarcinoma (grade III/III) | + | + | An.[e] |
| | | Uterus, myometrium with focally necrotic granulation tissue | | | An.[e] |
| D | 1990 | Uterus, endometrioid adenocarcinoma (Grade II/III) | + | – | + |
| | | Uterus, benign myometrium | | | – |
| E | 1990 | Uterus, adenosquamous carcinoma (grade III/III) | + | – | + |
| | | Uterus, benign myometrium | | | – |
| F | 1989 | Uterus, endometrioid adenocarcinoma (grade II/III) | + | – | + |
| | | Uterus, benign myometrium | | | – |
| G | 1992 | Uterus, endometrioid adenocarcinoma (grade I/III) | – | – | – |
| | | Uterus, benign myometrium | – | | |
| H | 1986 | Uterus, endometrioid adenocarcinoma (grade | + | – | + |

TABLE 3-continued

Analysis of clonality in endometrial hyperplasia and carcinoma

| Case | Year collected | Tissue diagnosis | Myometrial invasion | Metastatic dissemination[a] | Hpa II monoclonal[c] |
|---|---|---|---|---|---|
| I | 1990 | II/III) Uterus, benign myometrium Uterus, endometrioid adenocarcinoma (grade I/III) Uterus, benign myometrium | – | – | – – – |
| J | 1990 | Uterus, endometrioid adenocarcinoma (grade II/III) Uterus, benign myometrium | + | – | + – |

[a]Metastatic dissemination denotes cases with known local or distant metastases from the time of initial diagnosis through conclusion of the study (four of 94), as determined by case records of the Colorado Central Cancer Registry.
[b]Hpa II monoclonal denotes cases from which HG analysis of PCR products from Hpa II-treated genomic DNA showed marked attenuation or loss of signal for two of four heteroduplex bands.
[c]An. denotes cases from which PCR produced an anomalous pattern of PGK-1 amplification, precluding analysis of clonality.

TABLE 4

FISH analysis of X-chromosome content in poorly differentiated endometrioid adenocarcinoma (case C)

| Tissue diagnosis | Hybridization signals/nucleus (% cells) | | | |
|---|---|---|---|---|
| | 0 | 1 | 2 | 3 |
| Uterus endometrioid adenocarcinoma (grade III/III) | 5 | 55 | 38.5 | 1.5 |
| Uterus, focally necrotic granulation tissue | 10 | 56 | 33 | 1 |

---

We claim:

1. A method of determining whether a sample from a female individual contains cells of a neoplasm or cells of pseudoneoplastic or hyperplastic processes, said method comprising the steps of:

a) contacting DNA from said cells of said sample from a female individual with a cytosine-methylation specific endonuclease under digest conditions;

b) generating amplified fragments of a cytosine-methylation regulatable, polymorphic X chromosome gene of said DNA using primers that bracket a restriction site of said cytosine-methylation specific endonuclease and a polymorphic sequence in said gene;

c) generating heteroduplexes between said amplified fragments and a heteroduplex generator, wherein the sequence of said heteroduplex generator differs from the sequence of said amplified fragments by 1–5 nucleotide differences; and d) detecting the presence of a single species of heteroduplex or at least two species of heteroduplexes, wherein the presence of a single species of heteroduplex indicates amplified fragments from a clonal population of cells indicative of a neoplasm and the presence of at least two species of heteroduplexes indicates amplified fragments from a mosaic population of cells indicative of a non-neoplastic, pseudoneoplastic, or hyperplastic process.

2. The method of claim 1 wherein said neoplasm is adenocarcinoma and said pseudoneoplastic or hyperplastic process is endometrial hyperplasia with atypia.

3. The method of claim 1 wherein said cytosine-methylation specific endonuclease is HpaII.

4. The method of claim 1 wherein said amplified fragments are generated by polymerase chain reaction.

5. The method of claim 1 wherein said amplified fragments consist of 75–200 nucleotides.

6. The method of claim 1 wherein said amplified fragments consist of 100–600 nucleotides.

7. The method of claim 1 wherein said cytosine-methylation regulatable, polymorphic X chromosome gene is phosphoglycerate kinase-1.

8. The method of claim 1 wherein at least one primer is selected from the group consisting of: SEQ ID NO:1, SEQ ID NO:2, SEQ ID NO:3, and SEQ ID NO:4.

9. The method of claim 1 wherein said heteroduplex generator is SEQ ID NO:5.

10. The method of claim 1 wherein said single species of heteroduplex or said two species of heteroduplexes are detected by migrating said heteroduplexes in an electrophoresis matrix.

11. A method of claim 1 wherein said amplified fragments in b) are first amplified fragments which are used as substrates to generate a second amplified substrate that consists of 50–2000 nucleotides generated by amplifying a nucleotide sequence of said first amplified fragment using nested primers that bracket a restriction site of said cytosine-methylation specific endonuclease and a polymorphic sequence in said nucleotide sequence, wherein heteroduplexes generated in c) are between said second amplified fragments and said heteroduplex generators.

12. A kit comprising:

1) primers which bracket a methylation sensitive restriction site on a methylation regulated polymorphic X chromosome gene, wherein an amplified fragment is generated when DNA from a female individual is used as a substrate for said primer in a polymerase chain reactions and 2) a heteroduplex generator that forms heteroduplexes with said amplified fragment, said heteroduplex generator having a sequence which differs from the sequence of said amplified fragment by no more than 5 nucleotide sequence differences.

13. The kit of claim 12 further comprising one or more of the following:

1) a container of cytosine-methylation sensitive restriction endonuclease;

2) an intact matrix or materials useful for producing a matrix through which heteroduplexes can be migrated; and/or 3) instructions for using said kit to perform a method of distinguishing between neoplasms and pseudoneoplastic or hyperplastic processes.

14. The kit of claim 12 further comprising one or more of the following:

1) a container with a single species of heteroduplex formed by said heteroduplex generator and a sample that consists of amplified fragments from a first allele of said polymorphic gene;

2) a container with a single species of heteroduplex formed by said heteroduplex generator and a sample that consists of amplified fragments from a second allele of said polymorphic gene;

3) a container with two species of heteroduplexes formed by said heteroduplex generator and a sample that consists of amplified fragments from two different alleles of said polymorphic gene; and/or 4) DNA size markers.

15. The kit of claim 12 further comprising one or more of the following:

1) a photograph of a migration pattern produced by a single species of heteroduplex formed by said heteroduplex generator and a sample that consists of amplified fragments from a first allele of said polymorphic gene;

2) a photograph of a migration pattern produced by a single species of heteroduplex formed by said heteroduplex generator and a sample that consists of amplified fragments from a second allele of said polymorphic gene;

3) a photograph of a migration pattern produced by two species of heteroduplex formed by said heteroduplex generator and a sample that consists of amplified fragments from two different alleles of said polymorphic gene; and/or 4) DNA size markers.

16. A method of determining whether a fixed or embedded sample from a female individual contains cells of a neoplasm or cells of pseudoneoplastic or hyperplastic processes, said method comprising the steps of:

a) contacting DNA from said cells of said sample from a female individual with a cytosine-methylation specific endonuclease under digest conditions;

b) generating amplified fragments of a cytosine-methylation regulatable. polymorphic X chromosome gene of said DNA using primers that bracket a restriction site of said cytosine-methylation specific endonuclease and a polymorphic sequence in said gene;

c) generating heteroduplexes between said amplified fragments and a heteroduplex generator, wherein the sequence of said heteroduplex generator differs from the sequence of said amplified fragments by 1–5 nucleotide differences; and d) detecting the presence of a single species of heteroduplex or at least two species of heteroduplexes, wherein the presence of a single species of heteroduplex indicates amplified fragments from a clonal population of cells indicative of a neoplasm and the presence of at least two species of heteroduplexes indicates amplified fragments from a mosaic population of cells indicative of a non-neoplastic, pseudoneoplastic, or hyperplastic process.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CTGTTCCTGC CCGCGCGGTG TTCCGCATTC     30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear -continued (ii) MOLECULE TYPE: cDNA (xi) SEQUENCE DESCRIPTION: SEQ ID NO:2:

AGCTGGACGT TAAATTTAAG CGGGTCGTTA                                        30

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACGCCTGTTA CGTAAGCTCT GCAGGCCTCC                                        30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TACTCCTGAA GTTAAATCAA CATCCTCTTG                                        30

(2) INFORMATION FOR SEQ ID NO:5:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGCTGGACGT TAAAGGGAAG CGGGTCGTTA TGAGGTAATT CTGCACGTTT                  50
GCCCGCGTGC TCTCTGTGCT CTGTCGCAAA CCTCTTTGGC CGGAGCCGAC                 100
TTGTTCTCTC GTCTGCTCTA AGTTCTTTTA GCTTTTGGCT GGGCCCCAAG                 150
GGTCCTAGGC TTGGAGGGCG AGGCTGCTCA CGGGTTTGGT GGTTTCTAGC                 200
CGCATTTTCC CCAGCCCAGA AAGCACCCGA AGTCACCCTT CGGGATGGAT                 250
CCCACTGAGG AAGGGCTGAG ATTGCCGCTG GGACCCATTT TGTGCTTTTT                 300
CCTATTGGTG AAATGCAGTT CCGTGGCCTC CAGCTCCAGT CGGCGAGATG                 350
GGACTTAATG CTTATCCTGC AAATCTCTAG GCTTCACGGA AGGGACCTTG                 400
AAAGGTCATT TTACTTTCCC GTCGCAGCCA AATGAGAAAC GGCCCACATC                 450
TCACAGGTTC CTGCACAAAA GGATATTTTC CAAGAGGATG TTGATTTAAC                 500
TTCAGGAGTA                                                             510